US011607141B2

United States Patent
Yang

(10) Patent No.: US 11,607,141 B2
(45) Date of Patent: Mar. 21, 2023

(54) OPTICAL FIBER BLOOD PRESSURE CONTINUOUS DETECTION WRISTBAND AND WEARING APPARATUS

(71) Applicant: HUIJIA HEALTH LIFE TECHNOLOGY CO., LTD., Zhubei (CN)

(72) Inventor: Shuchen Yang, Zhubei (CN)

(73) Assignee: HUIJIA HEALTH LIFE TECHNOLOGY CO., LTD., Zhubei (CN)

( * ) Notice: Subject to any disclaimer, the term of this patent is extended or adjusted under 35 U.S.C. 154(b) by 986 days.

(21) Appl. No.: 16/406,506

(22) Filed: May 8, 2019

(65) Prior Publication Data
US 2019/0290138 A1     Sep. 26, 2019

Related U.S. Application Data

(63) Continuation-in-part of application No. 15/034,823, filed as application No. PCT/CN2015/071559 on Jan. 26, 2015, now abandoned.

(30) Foreign Application Priority Data

Dec. 31, 2014    (CN) .......................... 201410854008.4

(51) Int. Cl.
*A61B 5/021*     (2006.01)
*A61B 5/02*      (2006.01)
(Continued)

(52) U.S. Cl.
CPC ........ *A61B 5/02108* (2013.01); *A61B 5/0059* (2013.01); *A61B 5/02* (2013.01);
(Continued)

(58) Field of Classification Search
CPC ... A61B 5/02108; A61B 5/02; A61B 5/02438; A61B 5/681; A61B 5/0059; A61B 5/6826; A61B 2562/0266; A61B 2560/0223
See application file for complete search history.

(56) References Cited

U.S. PATENT DOCUMENTS

| 4,294,048 A | 10/1981 | Sutter |
| 5,056,884 A | 10/1991 | Quinlan, Jr. |

(Continued)

FOREIGN PATENT DOCUMENTS

| CN | 2721004 Y | 8/2005 |
| CN | 101288587 | 10/2008 |

(Continued)

OTHER PUBLICATIONS

Wang "Towards a Continuous Non-Invasive Cuffless Blood Pressure Monitoring System Using PPG:", IEEE circuits and systems magazine 1531-636X, 2018 (Year: 2018).*

(Continued)

*Primary Examiner* — Oommen Jacob
(74) *Attorney, Agent, or Firm* — Hamre, Schumann, Mueller & Larson, P.C.

(57) ABSTRACT

An optical fiber blood pressure continuous detection wristband, comprising: an optical fiber sensing assembly module, the optical fiber sensing assembly module includes a sensing band and an optical fiber configured to extend along the sensing band and form a sensing area to sense a pulse wave; the sensing band includes an inner layer configured to be placed adjacent to the wrist to be detected, and the outer surface of the inner layer is abutted against the optical fiber; an outer layer, the inner surface of the outer layer is provided with a first concave-convex structure with a corrugate shaped, the first concave-convex structure being abutted against the optical fiber; wherein a active space is formed (Continued)

between the sensing band and the inner watchband and configured for the radial artery to beat; a calibration assembly configured to continuously calibrate blood pressure values; and a signal process assembly.

17 Claims, 15 Drawing Sheets

(51) Int. Cl.
*A61B 5/00* (2006.01)
*A61B 5/024* (2006.01)
(52) U.S. Cl.
CPC .......... *A61B 5/02438* (2013.01); *A61B 5/681* (2013.01); *A61B 5/6826* (2013.01); *A61B 2562/0266* (2013.01)

(56) References Cited

U.S. PATENT DOCUMENTS

| | | | |
|---|---|---|---|
| 5,134,281 A * | 7/1992 | Bryenton | G01D 5/35374 |
| | | | 250/227.16 |
| 5,193,129 A | 3/1993 | Kramer | |
| 5,212,379 A | 5/1993 | Nafarrate et al. | |
| 5,241,300 A | 8/1993 | Bushmann | |
| 5,291,013 A | 3/1994 | Nafarrate et al. | |
| 5,293,039 A | 3/1994 | Mongiols | |
| 5,357,813 A | 10/1994 | Weinberger | |
| 5,868,677 A | 2/1999 | Iwanaga et al. | |
| 6,498,652 B1 | 12/2002 | Varshneya et al. | |
| 6,607,486 B1 | 8/2003 | Watson | |
| 6,816,266 B2 | 11/2004 | Varshneya et al. | |
| 7,747,386 B2 | 6/2010 | Hishida et al. | |
| 9,186,078 B2 | 11/2015 | Sohma et al. | |
| 9,360,351 B2 | 6/2016 | Van Thienen et al. | |
| 9,420,964 B2 | 8/2016 | Mitachi et al. | |
| 9,531,859 B2 * | 12/2016 | Tan | H04M 1/05 |
| 9,572,517 B2 | 2/2017 | Ng et al. | |
| 10,480,909 B1 * | 11/2019 | Brown | E05B 75/00 |
| 10,709,339 B1 * | 7/2020 | Lusted | A61B 5/282 |
| 10,984,645 B2 * | 4/2021 | Wojcik | G08B 21/22 |
| 2003/0095263 A1 | 5/2003 | Varshneya et al. | |
| 2007/0053647 A1 | 3/2007 | Hishida et al. | |
| 2008/0221488 A1 | 9/2008 | Kurono et al. | |
| 2010/0049010 A1 | 2/2010 | Goldreich | |
| 2011/0248853 A1 * | 10/2011 | Roper | G08B 21/0288 |
| | | | 340/573.4 |
| 2012/0203117 A1 | 8/2012 | Chen et al. | |
| 2013/0109931 A1 | 5/2013 | Ng et al. | |
| 2014/0270669 A1 | 9/2014 | Sohma et al. | |
| 2014/0298586 A1 | 10/2014 | Van Thienen et al. | |
| 2015/0098077 A1 * | 4/2015 | Findlay | G01K 11/32 |
| | | | 356/73.1 |
| 2015/0309535 A1 * | 10/2015 | Connor | A61B 5/1477 |
| | | | 361/679.03 |
| 2016/0015271 A1 | 1/2016 | Wang et al. | |
| 2016/0324431 A1 | 11/2016 | Ng et al. | |
| 2016/0338601 A1 * | 11/2016 | Yang | A61B 5/6826 |
| 2018/0059714 A1 * | 3/2018 | Martin | G06F 1/1635 |
| 2018/0294553 A1 * | 10/2018 | Lim | H01Q 5/35 |
| 2019/0290138 A1 * | 9/2019 | Yang | A61B 5/02108 |

FOREIGN PATENT DOCUMENTS

| | | |
|---|---|---|
| CN | 101288587 A | 10/2008 |
| CN | 102573615 | 7/2012 |
| CN | 102573615 A | 7/2012 |
| CN | 204468056 | 7/2015 |
| CN | 204468056 U | 7/2015 |
| JP | 08-000584 | 1/1996 |
| JP | 2008284001 | 11/2008 |
| JP | 2012065911 | 4/2012 |
| WO | 2008132690 A2 | 11/2008 |
| WO | 2013051602 | 4/2013 |
| WO | 2013180085 | 12/2013 |

OTHER PUBLICATIONS

Notice of Reasons for Refusal issued in corresponding Japanese Patent Application No. 2016-563189, dated Sep. 28, 2017, 11 pages, English translation.
International Search Report and Written Opinion (in English and Chinese) issue in PCT/CN2015/071559, dated Sep. 25, 2015, 18 pages provided.
First Office Action issued in Chinese Application No. CN201410854008.4 dated May 31, 2019, with English translation.

* cited by examiner

OPTICAL FIBER BLOOD PRESSURE CONTINUOUS DETECTION WRISTBAND AND WEARING APPARATUS

CROSS REFERENCE

This application is a continuation in part of U.S. Ser. No. 15/034,823 filed on Jan. 26, 2015, now pending, which is a National Stage Application of International Patent Application No. PCT/CN2012/087786, with an international filing date of Jan. 26, 2015, and further claims foreign priority benefits to Chinese Patent Application No. 201410854008.4, filed on Dec. 31, 2014. The contents of all of the aforementioned applications are incorporated herein by reference.

TECHNICAL FIELD

The present application relates to the technical field of blood detection, and particularly to an optical fiber blood pressure continuous detection wristband and a wearing apparatus.

BACKGROUND TECHNOLOGY

Nowadays, normally a non-invasive detecting method is provided for detecting blood. Non-invasive detecting mainly includes the stethoscopy method (Korotkoff-Sound Method) and the succussion method (Oscillography Method). The principle of the stethoscopy method is to collect Korotkoff sound. The whole apparatus includes an inflatable and deflatable cuff, a mercury manometer and a stethoscope. The principle of succussion is to utilize the oscillographic principle of pulse contour to determine the SBP (Systolic Blood Pressure) and the DBP (Diastolic Blood Pressure), which is widely used in most domestic and overseas non-invasive automated sphygmomanometers nowadays.

However, these both the two methods all need to inflate and deflate the cuff. The disadvantages are that: it is difficult to carry the apparatuses because each of them includes the cuff, the pump and the valve or the like and thus has a large volume. If the cuff is used frequently, the tissue and blood vessel beneath the cuff may be damaged because of being frequently pressed; because a certain time for inflating and deflating the cuff is needed, the continuous detection for blood pressure cannot be realized.

Moreover, the recent study result shows that non-cuff non-invasive blood pressure detecting detection is possible. It is a method that utilizes the transmission speed of a pulse wave to detect a blood pressure. The transmission speed of the pulse wave refers to the speed of the pulse wave transmits along the artery. Many study results show that: the pulse wave transmission speed is related to a blood pressure. A common way to detect the pulse wave transmission speed is to detect the pulse wave transmission time which is the time that needed for the pulse wave to transmit from the heart to radial artery. The pulse transmission time could be determined by utilizing a reference point on an electrocardiosignal and another reference point on a pulse wave detected on a peripheral arterial at during the same cardiac cycle. Pulse The pulse wave could be detected through an optical method. It is called as photoplethysmography. Photoplethysmography comprises lighting the light on the body tissue and detecting the reflected light, transmission light or scattered light on the body tissue. The light signal received by the photoelectric detector presents the variation of blood flow volume of the tissue.

However, the detecting device utilize pulse transmission time or speed to detect blood may have the following disadvantages: detecting the pulse wave transmission time needs an ECG (electrocardiograph) detecting device and a pulse wave detecting device, which means many detecting devices are needed; in addition, in order to detect the needed time of the pulse wave transmitted from the heart to the a reference point on radial artery precisely during detection, a subject cannot move freely. If the subject moves, the locating of the reference would be imprecise, then it may need to relocate the reference point. Hence, the present pulse wave detecting apparatus is not suitable for longtime continuous detecting and it only could be used in a clinic.

As disclosed on a patent with authorized announcement No. CN101288587, a strap human blood pressure non-invasive continuous detecting apparatus utilizes a sphere-shape pulse wave sensor probe to detect the pulse wave of a human wrist radial artery ensures a good contact between the probe and the human wrist radial artery by a compressing spring, and through the positioning of the slot and the olecroanon, guarantees that the repositioning would be precise and the wrist movement would be avoided during the continuous detecting process.

However, there is also such a problem: the area that contacts with the probe is the area where pulse wave sensor detects the pulse wave of the human radial artery, which is a point to point area detection. Therefore, when the strap human blood pressure non-invasive continuous detecting apparatus is used, the probe of the pulse wave sensor has to align with the human wrist radial artery and the slot has to align with the olecroanon. During the detecting process, if the strap moves inevitably due to the movement of the subject's wrist, the positioning of the probe and the human wrist radial artery will be dislocated. Therefore, it will cause the positioning imprecision of the human wrist radial artery relative to the strap human blood pressure non-invasive detecting apparatus, and the 24 hours non-invasive continuous detection for human blood pressure cannot be realized.

SUMMARY

An object of the present application is providing an optical fiber blood pressure continuous detection wristband, in order to solve the problems in existing blood detecting methods that there are complicated structures, it is difficult to carry, a subject's skin may be damaged, a subject cannot move freely, the positioning is imprecise, and it is unable to perform a continuous detection for a longtime.

In order to solve the above problem, the present application provides an optical fiber blood pressure continuous detection wristband for detecting a blood pressure, including:

a wristband assembly, configured to be worn on a wrist to be detected and comprising: an inner wristband and an outer wristband that are mutually engageable, wherein when the inner wristband and the outer wristband are fully engaged, an engaged portion of the inner wristband is configured to be placed adjacent to the wrist to be detected relative to the outer wristband;

an optical fiber sensing assembly module, disposed on a surface of the inner wristband away from the outer wristband; the optical fiber sensing assembly module includes a sensing band and an optical fiber configured to extend along the sensing band and form a sensing area to sense a pulse wave; the sensing band includes an inner layer having a first surface and a second surface opposite to the first surface, with the second surface being configured to be placed adjacent to the wrist to be detected, and the first surface being abutted against the optical fiber; and an outer layer having a third surface and a fourth surface opposite to the third surface, with the third surface being provided with a first concave-convex structure with a corrugate shaped, the first concave-convex structure being abutted against the optical fiber; wherein a space is formed between the sensing band and the inner wristband and configured for the radial artery to beat;

a calibration assembly, configured to detect a blood pressure of the wrist to be detected in conjunction with the optical fiber sensing assembly module, and configured to continuously calibrate a blood pressure value detected by the optical fiber sensing assembly module using one hand; and a signal process assembly, connected between the inner wristband and the outer wristband, and configured to convert a luminous decay signal generated by the decay of a light signal passing through the optical fiber into an electric charge so as to calculate the pulse wave.

In an embodiment of the present application, an outer surface of the sensing band is covered by a stretchable adjustable layer.

In an embodiment of the present application, the outer wristband is provided with a signal reinforcing area corresponding to the optical fiber sensing assembly module, and the signal reinforcing area is provided with a plurality of bulges protruding toward the inner wristband.

In an embodiment of the present application, the plurality of bulges are arranged in a regular array on the signal reinforcing area.

In an embodiment of the present application, the signal process assembly including:

a control circuit, configured to electrically connected to the calibration assembly;

an optical fiber connector portion comprising an output portion and an input portion;

an LED light source component; and an optical fiber sensing component;

The LED light source component is electrically connected to the control circuit via the input portion, and the optical fiber sensing component is electrically connected to the control circuit via the output portion.

In an embodiment of the present application, the signal process assembly further includes:

an optical detecting module, configured to receive the light decay signal of the optical fiber;

a signal calculating and processing module, configured to convert the light decay signal of the optical fiber into electric charge so as to calculate the pulse wave;

a blood pressure calibrating module, configured to process, analyze and calculate the pulse wave in order to obtain the blood pressure value;

a memory module, configured to store the blood pressure value; and a displaying module, configured to display the blood pressure value.

In an embodiment of the present application, the calibration assembly is arranged on the signal process assembly and includes:

a first electrode, disposed on an outer surface of the displaying module; and a second electrode, disposed on an inner surface of the signal process assembly and configured to be attached to the wrist to be detected, such that the first electrode, the second electrode and a subject form a closed loop for detecting electrocardiograph signals.

In an embodiment of the present application, the shape of the first concave-convex structure is one of a group of a triangular corrugated shape, a circular corrugated shape, a quadrate corrugated shape, and a trapezoidal corrugated shape, or any combination of the triangular corrugated shape, the circular corrugated shape, the quadrate corrugated shape, or the trapezoidal corrugated shape thereof.

In an embodiment of the present application, the outer surface of the inner layer is provided with a second concave-convex structure, the shape of the second concave-convex structure is one of a group of a triangular corrugated shape, a circular corrugated shape, a quadrate corrugated shape, and a trapezoidal corrugated shape, or any combination of the triangular corrugated shape, the circular corrugated shape, the quadrate corrugated shape, or the trapezoidal corrugated shape thereof.

In an embodiment of the present application, the optical fiber comprises optical fiber rows having a plurality of serially connected U-shaped or S-shaped fiber cable extended along the longitudinal direction or width direction of the sensing band.

In an embodiment of the present application, the optical fiber comprises optical fiber rows having a plurality of serially connected O-shaped fiber cable extended along the longitudinal direction or width direction of the sensing band.

In an embodiment of the present application, at least two optical fiber rows are superposed vertically, and bend parts of the fiber cable of the vertically superposed optical fiber cable rows are staggered.

In an embodiment of the present application, at least two optical fiber rows are superposed vertically, and bend parts of the fiber cable of the vertically superposed optical fiber cable rows are arranged in a criss-cross pattern.

The present application further provides a wearing apparatus, including: an optical fiber blood pressure continuous detection wristband and an electronic circuit module electrically connected to the optical fiber blood pressure continuous detection wristband, wherein the optical fiber blood pressure continuous detection wristband comprises:

a wristband assembly, configured to be worn on a wrist to be detected and comprising: an inner wristband and an outer wristband that are mutually engageable, wherein when the inner wristband and the outer wristband are fully engaged, an engaged portion of the inner wristband is configured to be placed adjacent to the wrist to be detected relative to the outer wristband;

an optical fiber sensing assembly module, disposed on a surface of the inner wristband away from the outer wristband; the optical fiber sensing assembly module includes a sensing band and an optical fiber configured to extend along the sensing band and form a sensing area to sense a pulse wave; the sensing band includes an inner layer having a first surface and a second surface opposite to the first surface, with the second surface being configured to be placed adjacent to the wrist to be detected, and the first surface being abutted against the optical fiber; and an outer layer having a third surface and a fourth surface opposite to the third surface, with the third surface being provided with a first concave-convex structure with a corrugate shaped, the first concave-convex structure being abutted against the optical fiber; wherein a space is formed between the sensing band and the inner wristband and configured for the radial artery to beat;

a calibration assembly, configured to detect a blood pressure of the wrist to be detected in conjunction with the optical fiber sensing assembly module, and configured to continuously calibrate a blood pressure value detected by the optical fiber sensing assembly module using one hand; and a signal process assembly, connected between the inner wristband and the outer wristband, and configured to convert a luminous decay signal generated by the decay of a light signal passing through the optical fiber into an electric charge so as to calculate the pulse wave.

In an embodiment of the present application, the electronic circuit module includes:

a display unit, configured for human-computer interaction and displaying the detected blood pressure value; and a calculating and processing module unit, configured to process light decay changes and estimate pulse pressure changes of the radial artery.

Compared with the prior art, the optical fiber blood pressure continuous detection wristband provided by the present application has the following advantages:

By arranging the wristband assembly and the optical fiber sensing assembly module disposed on the inner wristband, such that the sensing band of the optical fiber sensing assembly module can be worn on a wrist of a subject, which thus a 24 hours non-invasive continuous detecting for a human blood pressure can be realized; in addition, the inner surface of the inner layer of the sensing band is abutted against a surface of the optical fiber, and the inner surface of the outer layer of the sensing band is provided with a first concave-convex structure, and the first concave-convex structure is abutted against another surface of the optical fiber; such that the inner layer and the optical fiber can be placed more adjacent to the wrist to be detected, and the pulsation of the radial artery of the wrist to be detected can be converted into light signal more distinct, and then the light signal is converted into pulse wave via the signal processing assembly; in addition, the calibration assembly is arranged at the inner wristband, such that the calibration assembly can be real-time in contract with the wrist to be detected, and continuously calibrate to the blood pressure value can be realized. Besides, the continuously calibrate to the blood pressure value can be realize via only one hand; thereby, the accuracy of the detected blood pressure values can be ensured.

Therefore, compared with existing non-invasive detecting methods, the problems of large volume and being difficult to carry caused by including the cuff, the pump and the valve or the like structure can be avoid; the problems that the subject would feel discomfort because of the inflation and deflation of the cuff and the wrist tissues and blood vessels could be damaged because of the frequent compression from the cuff can also be avoided. The problem that the blood pressure continuous detection cannot be realized because the inflation and deflation of cuff need certain time can further be avoided. Compared with existing pulse wave detecting apparatuses, the problem that the positioning of the reference point may be inaccurate because the subject moves freely, and that the longtime and continuous detection cannot be realized can be also avoided.

Another object of the present application is to provide a wearing apparatus. It aims to solve the problem in existing blood detecting methods that there is a complicated structure, it is difficult to carry, a subject's skin may be damaged, the subject may be discomfort, the subject cannot move freely, the location is imprecise, and a continuous detection for a longtime cannot be realized.

In order to solve the above technical problems, the technical solution of the wearing apparatus provided by the application includes the above-described optical fiber continuous detection blood pressure wristband.

The wearing apparatus provided by the application has the following advantages compared to the prior art:

Because the wearing apparatus has an optical fiber continuous detection blood pressure wristband, when a person wears the wearing apparatus, the wrist or arm could move freely, and the 24 hours non-invasive continuous detection for the human blood pressure could be realized without repositioning.

DETAILED DESCRIPTION

Figure 1:
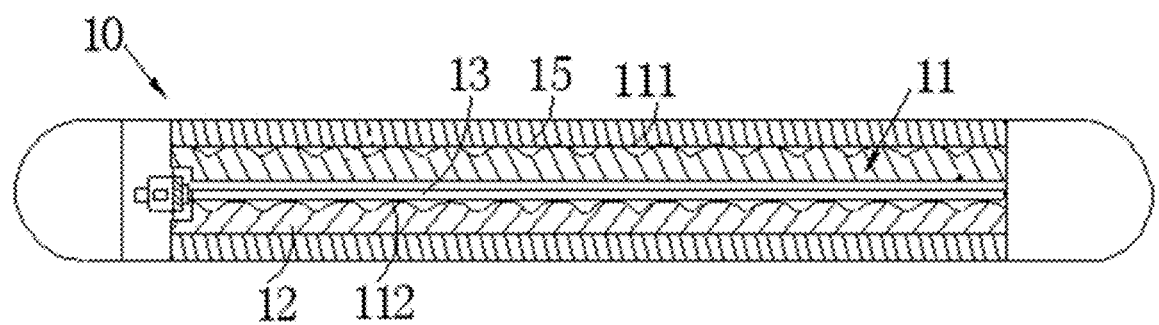
FIG. 1 is a cut-away view of an optical fiber continuous blood pressure wristband provided by one embodiment of the application.

In order to make the purpose, the technical solution and the advantages of the present application be clearer and more understandable, the present application will be further described in detail below with reference to accompanying figures and embodiments. It should be understood that the specific embodiments described herein are merely intended to illustrate but not to limit the present application.

It is noted that when a component is referred to as being "fixed to" or "disposed on" another component, it can be directly or indirectly on another component. When a component is referred to as being "connected to" another component, it can be directly or indirectly connected to another component.

In the description of the present application, it needs to be understood that, directions or location relationships indicated by terms such as "length", "width", "up", "down", "front", "rear", "left", "right", "vertical", "horizontal", "top", "bottom", "inside", "outside", and so on are the directions or location relationships shown in the accompanying figures, which are only intended to describe the present application conveniently and simplify the description, but not to indicate or imply that an indicated device or component must have specific locations or be constructed and manipulated according to specific locations; therefore, these terms shouldn't be considered as any limitation to the present application.

In addition, terms "the first" and "the second" are only used in describe purposes, and should not be considered as indicating or implying any relative importance, or impliedly indicating the number of indicated technical features. As such, technical feature(s) restricted by "the first" or "the second" can explicitly or impliedly comprise one or more such technical feature(s). In the description of the present application, "a plurality of" means two or more, unless there is additional explicit and specific limitation.

As shown in FIGS. 1-14, the present application provides an optical fiber 13 blood pressure continuous detection wristband, which configured to continuously detect the blood pressure of the subject, and including: a wristband assembly, configured to be worn on a wrist to be detected and including: an inner wristband 22 and an outer wristband 21 that are mutually engageable, wherein the inner wristband 22 is configured to be placed adjacent to the wrist to be detected, and a part of the outer wristband 21 is engaged with the inner wristband 22, and the other part is in contract with the wrist to be detected. The optical fiber 13 blood pressure continuous detection wristband further includes an optical fiber 13 sensing assembly module, disposed on the inner wristband 22 and configured to protrude outwardly along a surface of the inner wristband 22 away from the outer wristband 21, such that the optical fiber 13 sensing assembly module is configured to be placed adjacent to the radial artery of the wrist to be detected.

The optical fiber 13 sensing assembly module includes a sensing band 10 and an optical fiber 13 configured to extend along the sensing band 10 and form a sensing area to sense a pulse wave; wherein the sensing band 10 includes an inner layer 11 having an inner surface and an outer surface, wherein the inner layer 11 is configured to be placed adjacent to the wrist to be detected, and the outer surface of the inner layer 11 is abutted against the optical fiber 13; an outer layer 12 having an inner surface and an outer surface, the inner surface of the outer layer 12 is provided with a first concave-convex structure 112 with a corrugate shaped, the first concave-convex structure 112 being abutted against the optical fiber 13; wherein a active space 24 is formed between the sensing band 10 and the inner wristband 22 and configured for the radial artery to beat.

Whilst, in the present application, the sensing band 10 is generally a flexible band and can vary as the shape of the inner wristband 22 changes. When the wristband assembly is worn on the wrist to be detected, the sensing band 10 is invariably placed adjacent to an area where the radial artery of the wrist to be detected is located. So that when the subject moves, and the sensing band 10 is rotated or displaced on the wrist to be detected, the sensing area can sense the pulse wave of the wrist to be detected, that is, the sensing band 10 does not require special positioning.

The optical fiber 13 blood pressure continuous detection wristband further includes a calibration assembly 223, arranged at the inner wristband 22 and configured to detect a blood pressure of the wrist to be detected in conjunction with the optical fiber 13 sensing assembly module, and configured to continuously calibrate a blood pressure value detected by the optical fiber 13 sensing assembly module using one hand.

The optical fiber 13 blood pressure continuous detection wristband further includes a signal process assembly 14, connected between the inner wristband and the outer wristband, and configured to convert a luminous decay signal generated by the decay of a light signal passing through the optical fiber 13 into an electric charge so as to calculate the pulse wave.

Figure 2:
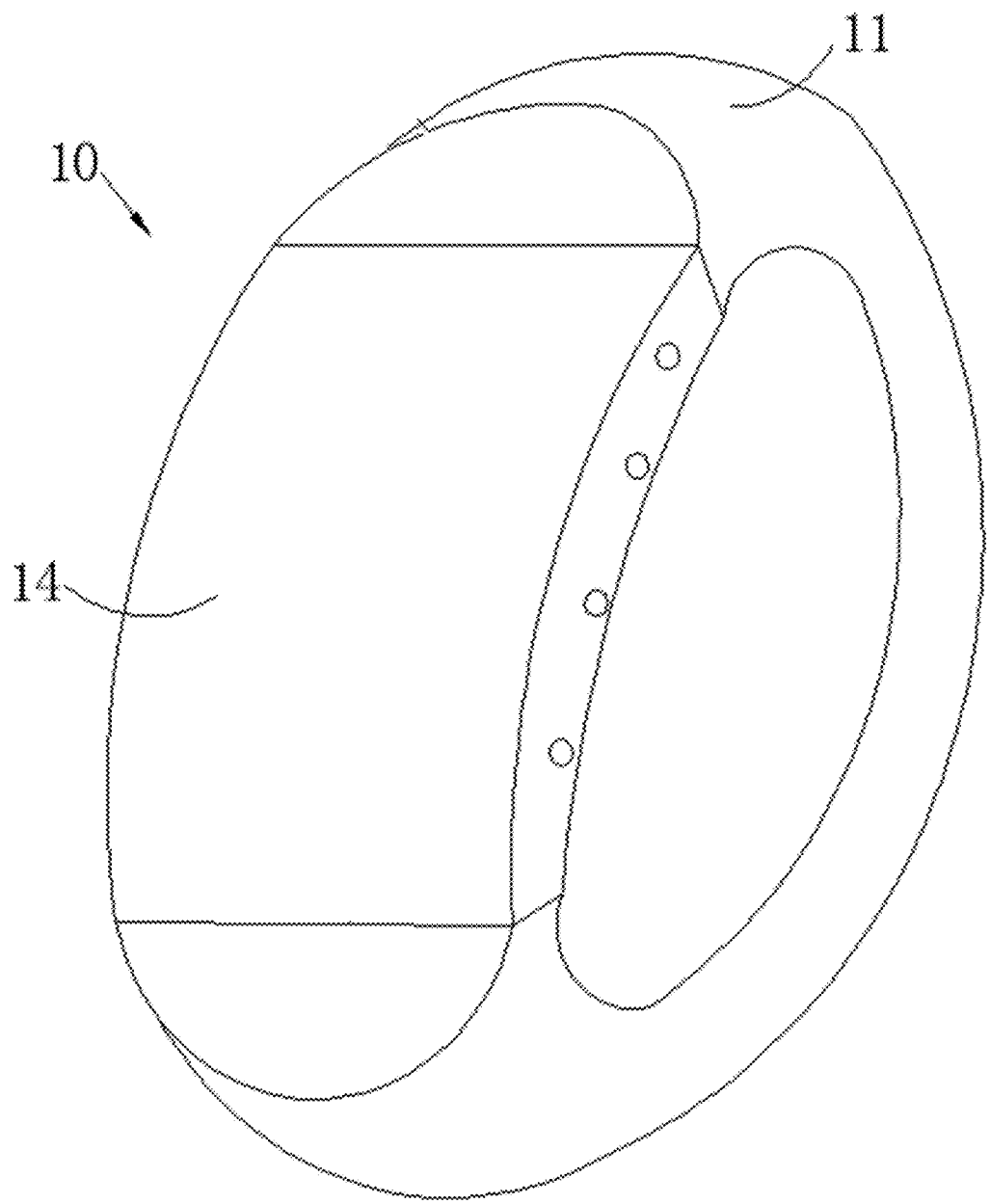
FIG. 2 is a perspective structural schematic view of the optical fiber continuous blood pressure wristband provided by the embodiment of the application.

It should be noted that, as shown in FIG. 1 and FIG. 2, the reason why the sensing area could sense the pulse wave is that the fluctuation of the pulse of the artery would provide a fluctuant pressure on the sensing band 10. Correspondingly, the optical fiber 13 arranged between the inner layer 11 and the outer layer 12 will deform due to the fluctuant pressure. Because of the deformation of the optical fiber 13, the transmission of the light signal in the optical fiber 13 would generate larger refraction, reflection, scattering and the decaying variation. One end of the sensing band 10 is provided with a signal process assembly 14 which communicates with optical fiber 13. At the moment, the light decaying signal of the optical fiber 13 is transmitted to signal process assembly 14 through communication. signal process assembly 14 transforms the light decaying signal into charge unit. Then the charge unit will be calculated into a pulse wave. Finally, the pulse wave is processed, analyzed and calculated to obtain the blood pressure value.

In an embodiment of the present application, an outer surface of the sensing band 10 is covered by a stretchable adjustable layer 15. In this way, the sensing band 10 can be worn on different human wrists. Therefore, the sensing band 10 is worn on the wrist securely. During detecting the blood pressure, even the subject moves, the dislocation between the sensing band 10 and the human wrist radial artery would not be prone to occur and there is no need to reposition the sensing band 10, so that a 24 hours non-invasive continuous detection for a human blood pressure can be realized, which has high stability and precision.

It should be noted that, the material of the sensing band 10 is soft material, such as silicone.

In an optional embodiment of the special structure of the sensing band 10 of the present application, as shown in FIGS. 1 and 2, in order to increase the elastic contact stress of the inner layer 11 of the sensing band 10 on the detected surface of the radial artery of the wrist to be detected, the inner surface of the outer layer 12 is provided with a corrugated first concave-convex structure 112, such that the first concave-convex structure 112 makes the inner layer 11 and the optical fiber 13 more attached to the wrist to be detected, such that the sensing band 10 positioned to the wrist to be detected more steadily, and the positioning change is not easily caused by the movement of the wrist of the subject, thereby the continuous and accurate detection of blood pressure can be ensured. In addition, the gap between the first concave-convex structure 112 and the optical fiber 13 also forms another active space for the radial artery to beat.

As shown in FIGS. 1 and 2, further, in order to increase the elastic contact stress of the inner layer 11 of the sensing band 10 on the detected surface of the radial artery of the wrist to be detected, the outer surface of the inner layer 11 may further forms a corrugated second concave-convex structure. In this way, when the sensing band 10 is worn on the wrist of the human body, the second concave-convex structure will abut against the adjustable layer 15 such that the inner layer 11 can be more attached to the wrist to be detected, the first concave-convex structure 112 apply a stress to the optical fiber 13, such that the contraction between the optical fiber 13 and the wrist to be detected can be ensured, thereby the positioning change is not easily caused by the movement of the wrist of the subject, and the continuous and accurate detection of blood pressure can be ensured.

Compared with he prior art, the optical fiber 13 blood pressure continuous detection wristband provided by the present application has the following advantages:

By arranging the wristband assembly and the optical fiber 13 sensing assembly module disposed on the inner wristband 22, such that the sensing band 10 of the optical fiber 13 sensing assembly module can be worn on a wrist of a subject, which thus a 24 hours non-invasive continuous detecting for a human blood pressure can be realized; in addition, the inner surface of the inner layer 11 of the sensing band 10 is abutted against a surface of the optical fiber 13, and the inner surface of the outer layer 12 of the sensing band 10 is provided with a first concave-convex structure 112, and the first concave-convex structure 112 is abutted against another surface of the optical fiber 13; such that the inner layer 11 and the optical fiber 13 can be placed more adjacent to the wrist to be detected, and the pulsation of the radial artery of the wrist to be detected can be converted into light signal more distinct, and then the light signal is converted into pulse wave via the signal processing assembly; in addition, the calibration assembly 223 is arranged at the inner wristband 22, such that the calibration assembly 223 can be real-time in contract with the wrist to be detected, and continuously calibrate to the blood pressure value can be realized. Besides, the continuously calibrate to the blood pressure value can be realize via only one hand; thereby, the accuracy of the detected blood pressure values can be ensured.

Therefore, compared with existing non-invasive detecting methods, the problems of large volume and being difficult to carry caused by including the cuff, the pump and the valve or the like structure can be avoid; the problems that the subject would feel discomfort because of the inflation and deflation of the cuff and the wrist tissues and blood vessels could be damaged because of the frequent compression from the cuff can also be avoided. The problem that the blood pressure continuous detection cannot be realized because the inflation and deflation of cuff need certain time can further be avoided. Compared with existing pulse wave detecting apparatuses, the problem that the positioning of the reference point may be inaccurate because the subject moves freely, and that the longtime and continuous detection cannot be realized can be also avoided.

Specifically, as shown in FIG. 1, the shape of the first convex-concave structure is one of a triangular corrugated shape, a circular corrugated shape, a quadrate corrugated shape, and a trapezoidal corrugated shape, or any combination of the triangular corrugated shape, the circular corrugated shape, the quadrate corrugated shape, or the trapezoidal corrugated shape. In like manner, the shape of the second concave-convex structure is similar to the shape of the first concave-convex structure 112. The shapes of the second concave-convex structure and the first concave-convex structure 112 only need to meet the requirement of being able to abut against the detected surface.

Figure 3:
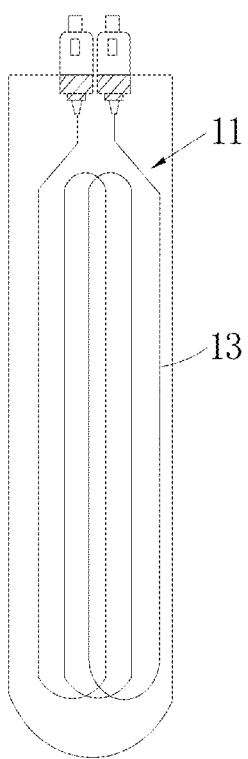
FIG. 3 is a layout of a first embodiment of the arrangement of the optical fiber of the optical fiber continuous detection blood pressure wristband on the sensing band provided by the embodiment of the application.
Figure 4:
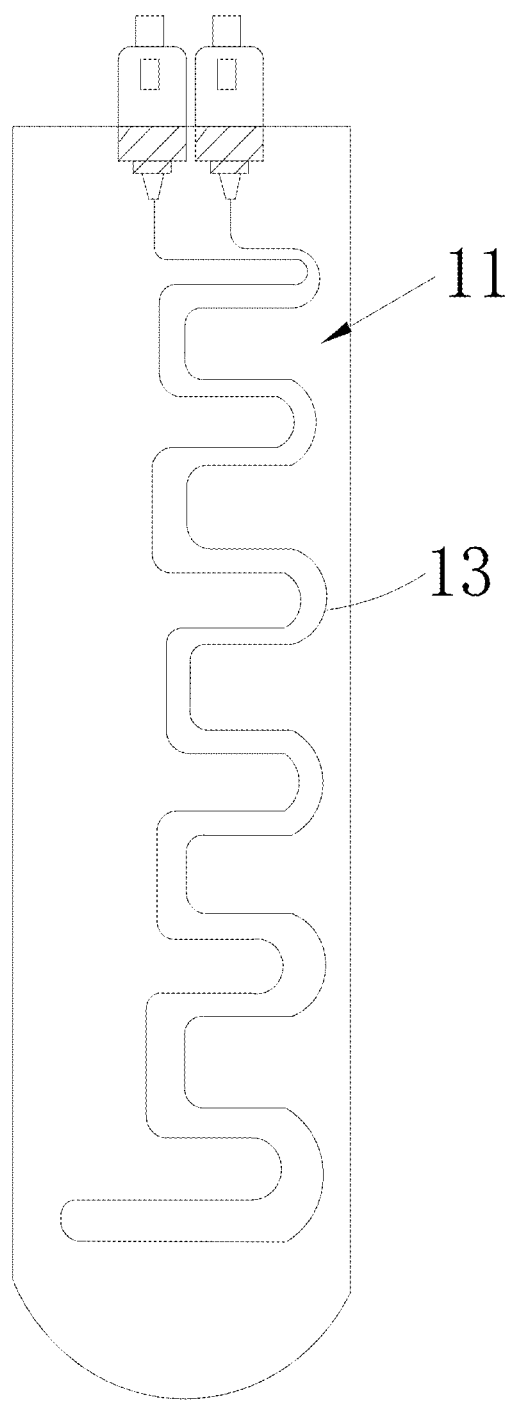
FIG. 4 is another layout of the first embodiment of the arrangement of the optical fiber of the optical fiber continuous detection blood pressure wristband on the sensing band provided by the embodiment of the application.

Specifically, the first embodiment about the specific arrangement of the optical fiber 13 which is located between the inner layer 11 and the outer layer 12, as shown in FIG. 3 and FIG. 4, the optical fiber 13 includes an optical fiber 13 which has many U-shape concatenated cablings extending along the longitudinal direction or width direction of the sensing band 10.

Figure 6:
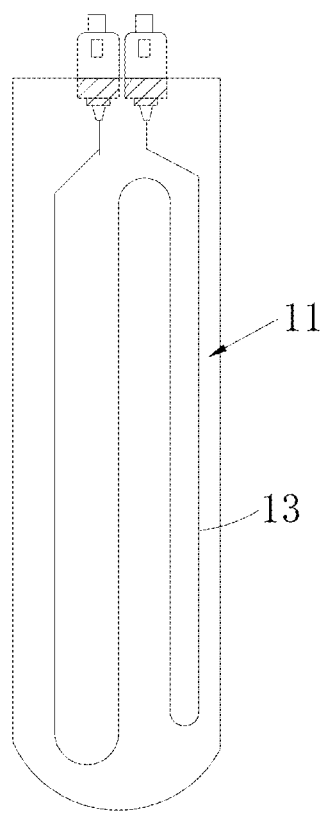
FIG. 6 is a layout of a second embodiment of the arrangement of the optical fiber of the optical fiber continuous detection blood pressure wristband on the sensing band provided by the embodiment of the application.

A second embodiment about the specific arrangement of the optical fiber 13 located between the inner layer 11 and the outer layer 12, as shown in FIG. 6, the optical fiber 13 includes an optical fiber 13 which has many S-shape concatenated cablings extending along the longitudinal direction or width direction of the sensing band 10.

Figure 7:
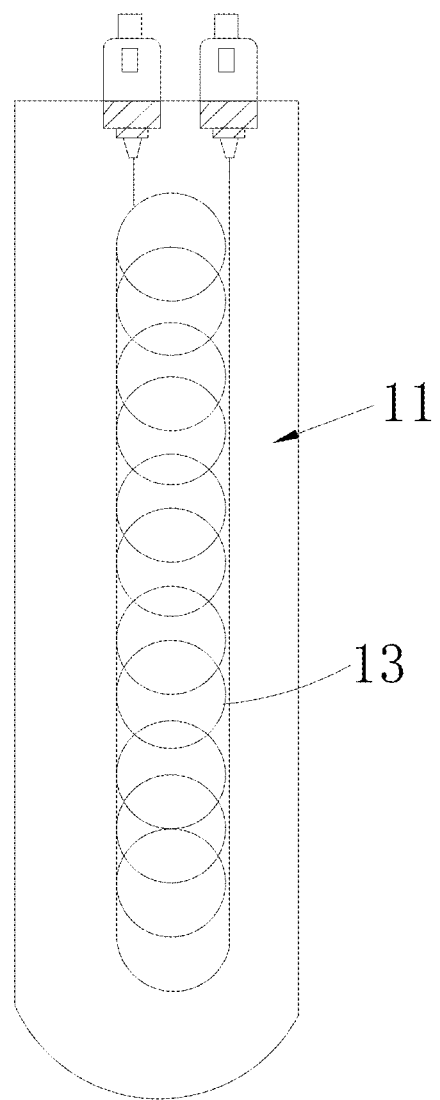
FIG. 7 is a layout of a third embodiment of the arrangement of the optical fiber of the optical fiber continuous detection blood pressure wristband on the sensing band provided by the embodiment of the application.
Figure 8:
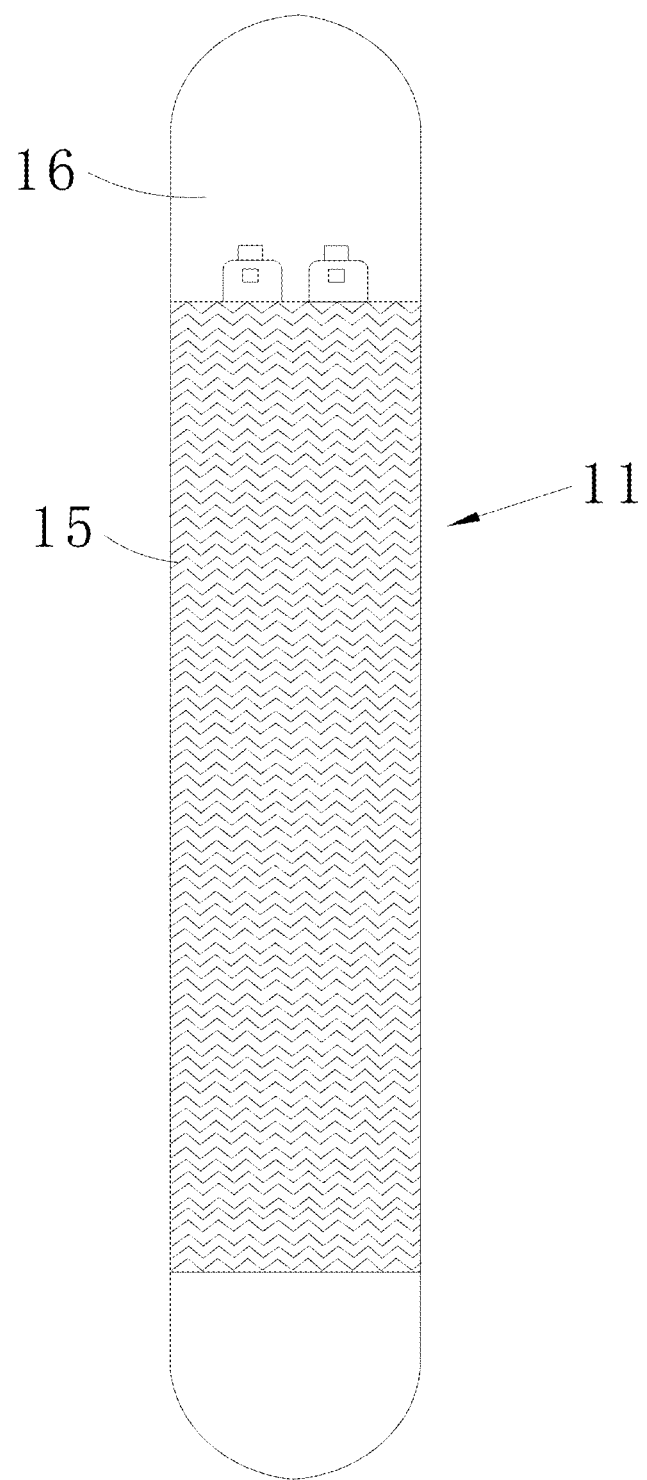
FIG. 8 is a rear view of the optical fiber continuous detection blood pressure wristband which not includes a signal process assembly provided by the embodiment of the application.
Figure 9:
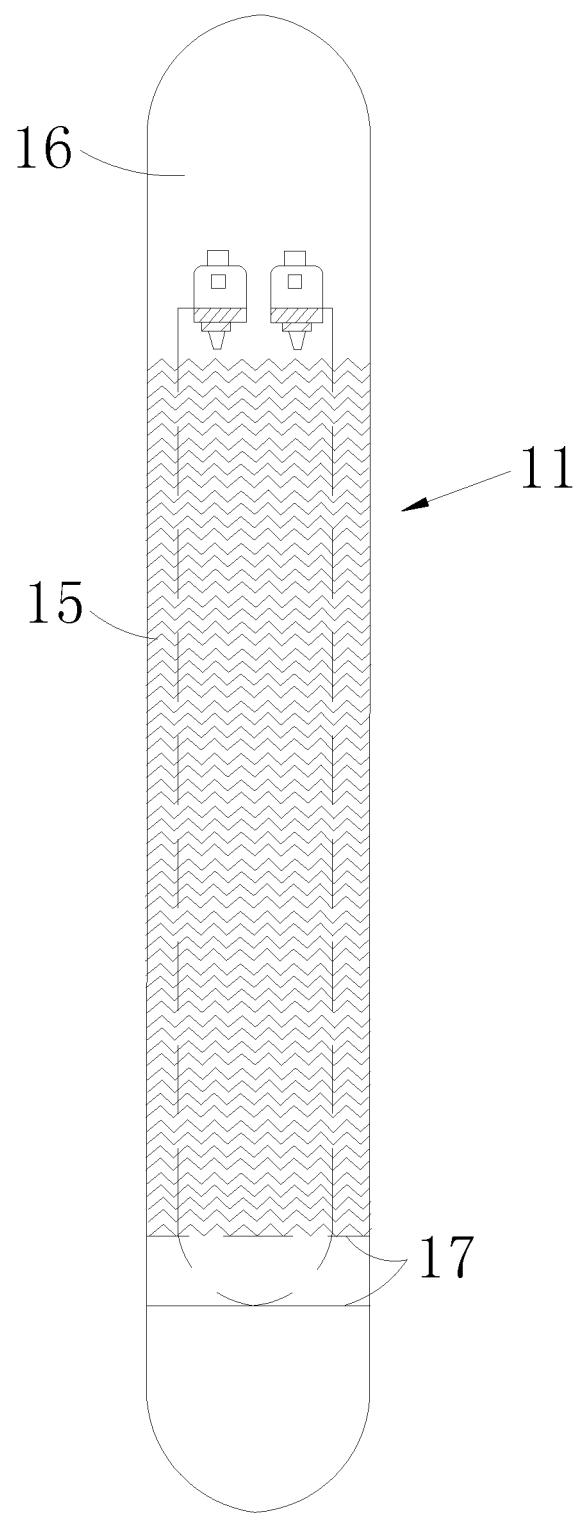
FIG. 9 is another rear view of the optical fiber continuous detection blood pressure wristband which not includes the signal process assembly provided by the embodiment of the application.

A third embodiment about the specific arrangement of the optical fiber 13 located between the inner layer 11 and the outer layer 12, as shown in FIG. 7, the optical fiber 13 includes an optical fiber 13 which has many O-shape concatenated cablings extending along the longitudinal direction or width direction of the sensing band 10.

Figure 5:
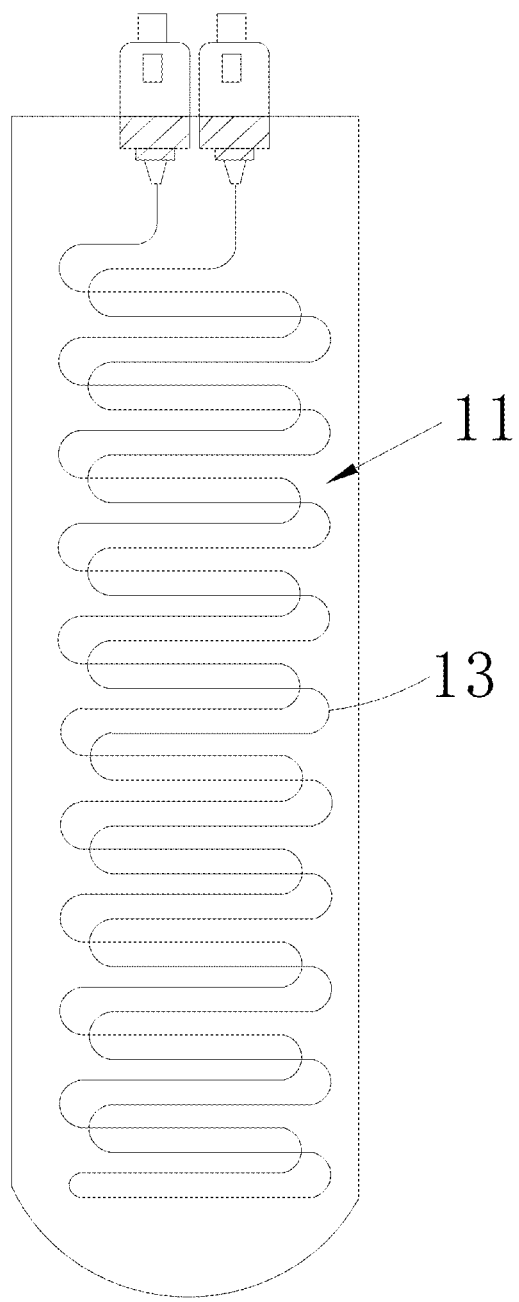
FIG. 5 is a layout of a fourth embodiment of the arrangement of the optical fiber of the optical fiber continuous detection blood pressure wristband on the sensing band provided by the embodiment of the application.

A fourth embodiment about the specific arrangement of the optical fiber 13 located between the inner layer 11 and the outer layer 12, as shown in FIG. 5, at least two optical fiber 13 rows are superposed vertically, and bending portions of the cablings of the two vertically superposed and placed adjacent optical fiber 13 rows are staggered.

Figure 10:
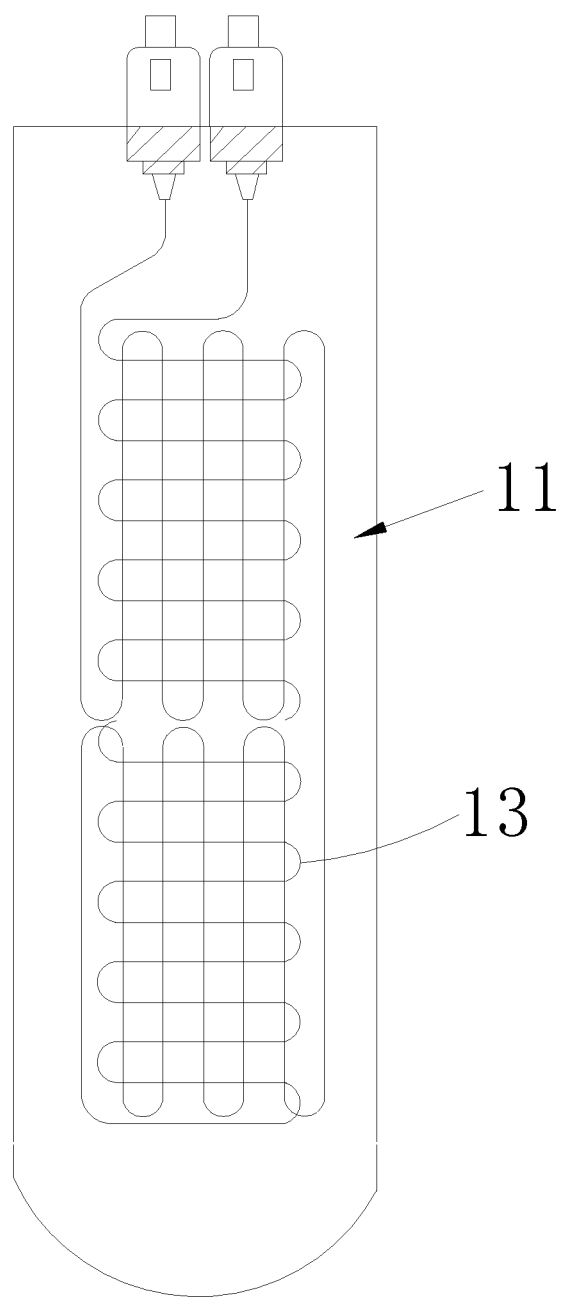
FIG. 10 is a layout of a fifth embodiment of the arrangement on the sensing band of the optical fiber of the optical fiber continuous detection blood pressure wristband provided by the embodiment of the application.

The fifth embodiment about the specific arrangement of the optical fiber 13 located between the inner layer 11 and the outer layer 12, as shown in FIG. 10, at least two optical fiber 13 rows are superposed vertically, and bending portions of the cablings of the two vertically superposed and placed adjacent optical fiber 13 rows are staggered transversely and longitudinally.

Whichever one of the above five embodiments is adopted by the arrangement of the optical fiber 13, the ribbon sensing area of the optical fiber 13 extending along the sensing band 10 is intensive and uniform. In this way, it helps increase the sensing sensitivity of the sensing area to the pulse wave of the human wrist radial artery. No matter what the contact stress from the inner layer 11 of the sensing band 10 to the detected surface is inadequate or decreases, the sensing area could sense the pulse wave of the radial artery sensitively and helps improve the precision of blood detecting.

In an embodiment of the present application, the outer wristband 21 is provided with a signal reinforcing area 211 corresponding to the optical fiber 13 sensing assembly module, the signal reinforcing area 211 corresponding to the active space, and the signal reinforcing area 211 is provided with a plurality of bulges 2111 protruding toward the inner wristband 22.

Figure 12:
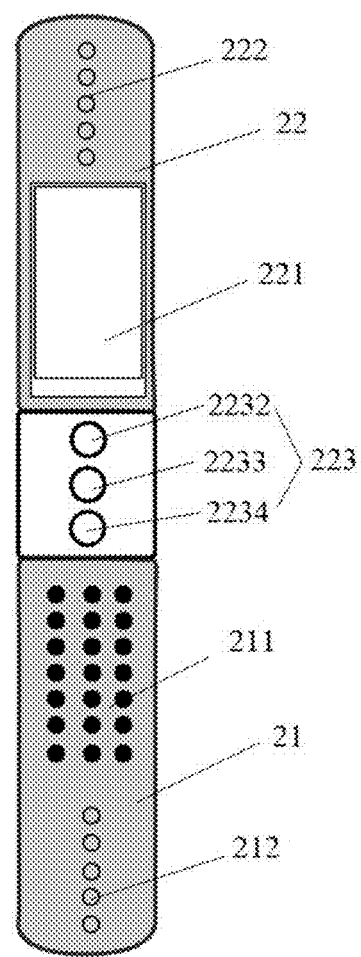
FIG. 12 is a schematic structural view of wristband assembly in a optical fiber continuous detection blood pressure wristband provided by the embodiment of the application.
Figure 13:
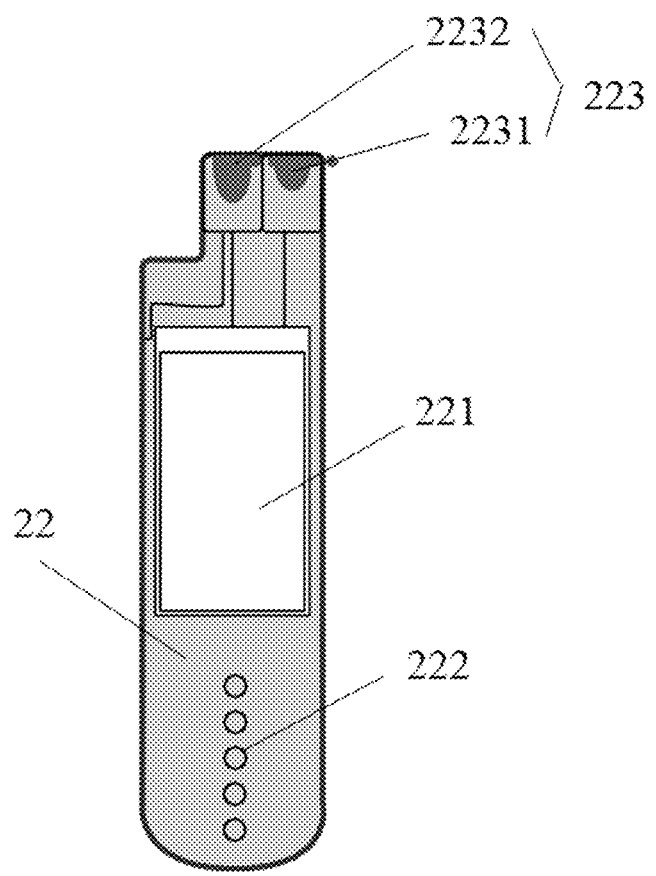
FIG. 13 is a schematic structural view of an inner wristband of the wristband assembly provided by the embodiment of the application.
Figure 14:
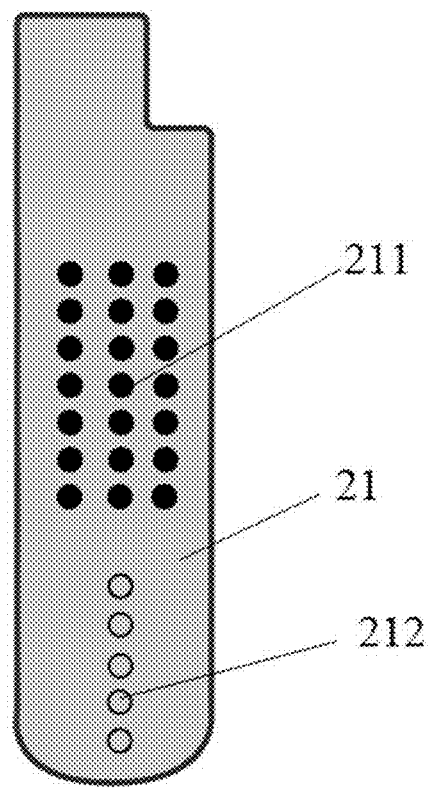
FIG. 14 is a schematic structural view of an outer wristband of the wristband assembly provided by the embodiment of the application.

In the present application, as shown in FIGS. 12-14 the inner wristband 22 includes a sensing area 221 configured to connect the sensing band 10 and a first engagement area 222 configured to engage with the outer wristband 21; accordingly, the outer wristband 21 includes the signal reinforcing area 211 arranged towards the sensing area 221 and a second engagement area 212 configured to engage with the first engagement area 222. In the present embodiment, when the first engagement area 222 is engaged with the second engagement area 212, the signal reinforcing area 211 is abutted against the sensing area of the sensing band 10.

In the present application, optionally, the signal reinforcing area 211 is consisted of a plurality of bulges 2111 protruding toward the inner wristband 22. The design of the plurality of bulges 2111 can assist enhancing the sensitivity the first concave-convex structure 112, or the first concave-convex structure 112 and the second concave-convex structure to the pulse wave of the radial artery of the wrist to be detected.

Preferably, in the present application, the plurality of bulges 2111 are arranged in a regular array on the signal reinforcing area 211. Alternatively, the plurality of bulges 2111 are arranged in a circular or other shape on the signal reinforcing area 211. The number of bulges 2111 is not limited herein, and the specific number can be set according to the length of the actual wristband.

In an embodiment of the present application, the signal process assembly 14 includes: a control circuit, configured to electrically connected to the calibration assembly 223; an optical fiber 13 connector portion comprising an output portion and an input portion; a LED light source component; and an optical fiber 13 sensing component; and the LED light source component is electrically connected to the control circuit via the input portion, and the optical fiber 13 sensing component is electrically connected to the control circuit via the output portion. Thereby, the signal process assembly 14 completes the detection of the light decay by the cooperation of the LED light source component and the optical fiber 13 sensing component, and converts the light decay signal into a pulse wave, and finally converts into a blood pressure value.

The preferred embodiment about the specific structure of the signal process assembly 14. Further, the signal process assembly 14 includes an optical detecting module (not shown) used to receive the light decay signal of the optical fiber 13; a signal calculating and processing module (not shown) used to transform the light decaying signal into the charge unit so as to calculate the pulse wave; a blood pressure calibrating module (not shown) used to process, analyze and calculate the pulse wave so as to obtain the blood pressure value; a memory module used to store the blood pressure value; and a displaying module (not shown) used to display the blood pressure value.

It should be noted that, the displaying module can display by a fixed terminal or a mobile terminal. For example, the display module can be a computer screen, a laptop screen, a cellphone screen or an Ipad screen, etc.

Specifically, the signal process assembly 14 includes a communicating module (not shown) which transmits the blood pressure value signal and other signals to the fixed terminal or mobile terminal through wire communication or wireless communication. Specifically, wire communication can communicate with the terminal through ports and wireless communication can communicate with the terminal through a bluetooth module. A fixed terminal or a mobile terminal, such as a computer or a cellphone can record, stores the detected blood pressure value or other values, thereby forming a longterm continuous recording and creating a searchable report. Moreover, the report containing blood pressure value or other values can be stired to the cloud, then the report can be downloaded from the cloud as medical diagnostic reference.

In an embodiment of the present application, the calibration assembly 223 is configured to detect a blood pressure of the wrist to be detected in conjunction with the optical fiber 13 sensing assembly module, and configured to continuously calibrate a blood pressure value detected by the optical fiber 13 sensing assembly module using one hand.

Figure 11:
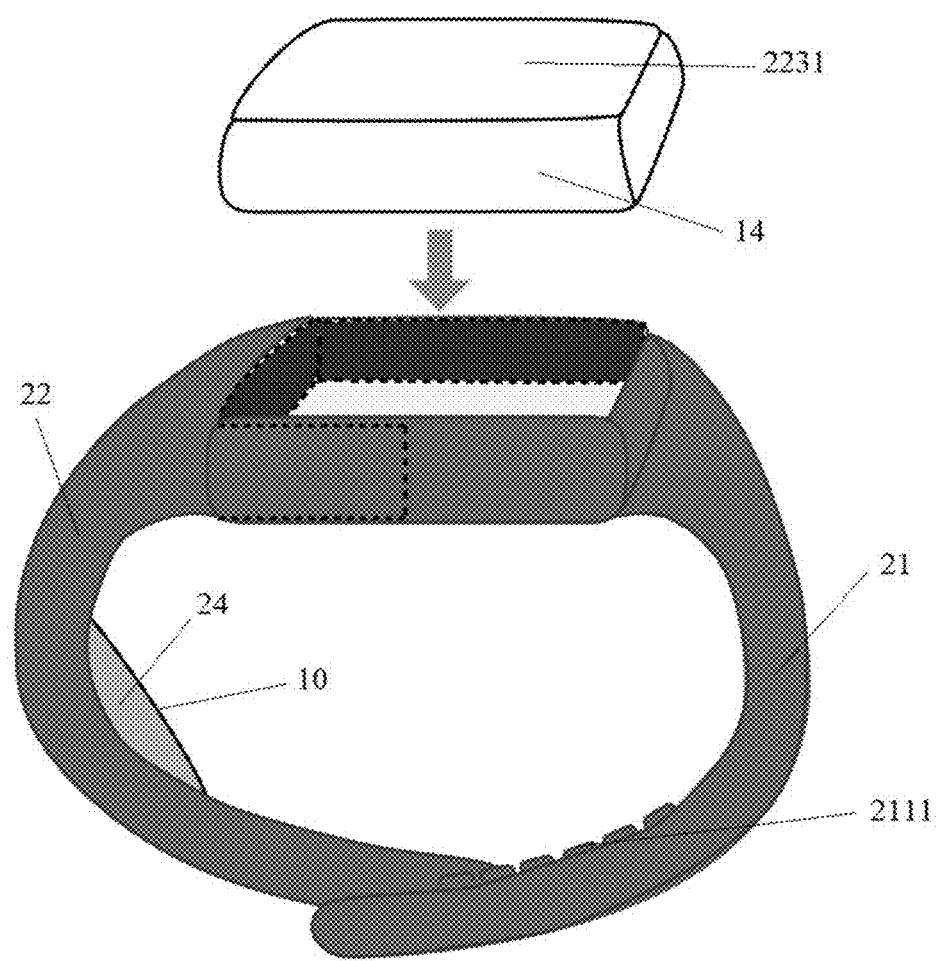
FIG. 11 is a schematic structural view of an optical fiber continuous detection blood pressure wristband provided by the embodiment of the application.

In the present embodiment, as shown in FIGS. 11 and 12, the calibration assembly 223 includes: a first electrode 2231, disposed on an outer surface of the display module and configured to be attached to another hand of the subject; and a second electrode, disposed on an inner surface of the signal process assembly 14 and configured to be attached to the wrist to be detected, such that the first electrode 2231, the second electrode and a subject form a closed loop for detecting electrocardiograph signals.

Specifically, the second electrode includes: a loop electrode 2232, directly in contract with the wrist to be detected and configured to form a closed loop for detecting electrocardiograph signals with the first electrode 2231 and the subject; a third electrode 2233, directly in contract with the wrist to be detected and configured to detect electrocardiograph characteristic signal separately, wherein the electrocardiograph characteristic signal can be obtained via phase-delayed by the processing circuit and subtracted from the radial artery pulse wave signal; a fourth electrode 2234, configured to be a reference electrode.

Wherein, the first electrode 2231 and the loop electrode 2232 are in contract with two hand of the subject respectively, with the fourth electrode 2234 as a reference, and form a loop with the subject, to detect a lead-electrocardiograph signal; which is the first method to detect the electrocardiograph signal.

In addition, the third electrode 2233 is configured to detect electrocardiograph characteristic signal separately, which detects a radial artery pulse wave signal, and then via phase-delayed by the processing circuit and subtracted from the radial artery pulse wave signal to obtain electrocardiograph characteristic signals, at the same time, the distance between the ECG and the pulse wave signal can be used to estimate the pulse wave velocity, which is another method to detect the electrocardiograph signal. Therefore, not only directly detecting the value of the radial artery pressure, the device can also estimate the blood pressure value through the pulse wave velocity.

Figure 15:
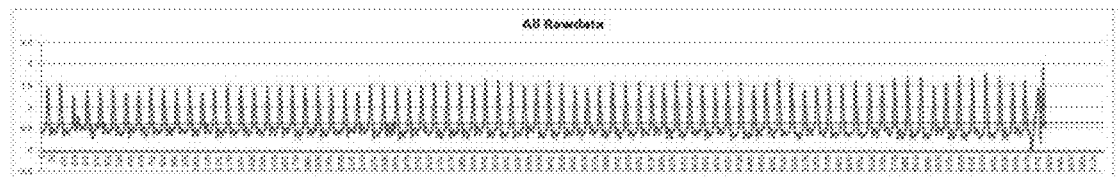
FIG. 15 is a diagram showing a radial artery pulse wave signal detected via the optical fiber continuous detection blood pressure wristband provided by the embodiment of the application.

In the present application, the difference of detection between the optical fiber 13 blood pressure continuous detection wristband and the conventional electronic sphygmomanometer to state the feasibility of the embodiments, in particular:

Firstly, wearing the optical fiber 13 blood pressure continuous detection wristband of the present application on the wrist to be detected to detect the radial artery pulse wave signal, as shown in FIG. 15. It can be seen that the radial artery pulse wave signal detected by the optical fiber 13 blood pressure continuous detection wristband is balanced and stable.

Secondly, using the conventional electronic sphygmomanometer to detect the contraction and diastolic pressure of the wrist to be detected.

Figure 16:
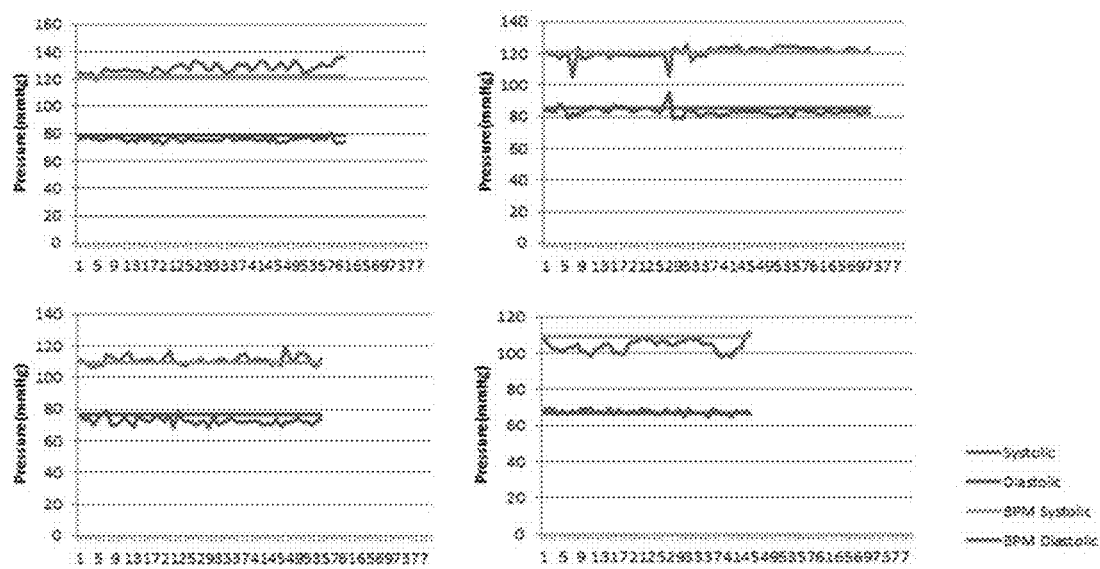
FIG. 16 is a diagram showing a comparison between the optical fiber continuous detection blood pressure wristband provided by the embodiment of the application and a conventional electronic sphygmomanometer.

Then using the optical fiber 13 blood pressure continuous detection wristband to detect the contraction and diastolic pressure of the wrist to be detected; comparing the difference between the two detected values, and drawing the FIG. 16. Wherein the blue curve is the estimated value of the optical fiber 13 pulsation systolic pressure; the green curve is the detected systolic pressure of the electronic sphygmomanometer; the red curve is the estimated value of the optical fiber 13 pulsation diastolic pressure; the purple curve is the detected diastolic pressure of the electronic sphygmomanometer.

The experimental data comparison is as follows

| Subject | Subject1 | Subject2 | Subject3 | Subject4 |
|---|---|---|---|---|
| Systolic pressure | 146 | 108 | 129 | 106 |
| Estimated systolic pressure | 143 | 108 | 129 | 105 |
| Difference | 3 | 0 | 0 | 1 |
| diastolic pressure | 99 | 69 | 75 | 66 |
| Estimated diastolic pressure | 100 | 71 | 78 | 69 |
| Difference | 1 | 2 | 3 | 3 |

After the experiment and calculation, the estimated systolic pressure and diastolic pressure are compared with the values detected by the electronic sphygmomanometer. The maximum difference is 3 mmHg and the minimum is 1 mmHg. Based on the above results, it is possible to preliminarily verify the feasibility of the detection of the radial artery pulsation of the wrist by the optical fiber 13 and the accuracy of the blood pressure estimation. Finally, the difference between the optical fiber 13 blood pressure continuous detection wristband and the electronic sphygmomanometer can be compensated by the calibration of the calibration assembly 223.

The present application further provides a wearing apparatus, including: an optical fiber 13 blood pressure continuous detection wristband described above and an electronic circuit module electrically connected to the optical fiber 13 blood pressure continuous detection wristband.

The electronic circuit module includes: a display unit, configured for human-computer interaction and displaying the detected blood pressure value; and a calculating and processing module unit, configured to process light decay changes and estimate pulse pressure changes of the radial artery.

Specifically, the electronic circuit module further includes an optical detecting module (not shown) used to receive the light decay signal of the optical fiber 13; a signal calculating and processing module (not shown) used to transform the light decaying signal into the charge unit so as to calculate the pulse wave; a blood pressure calibrating module (not shown) used to process, analyze and calculate the pulse wave so as to obtain the blood pressure value; a memory module used to store the blood pressure value; and a displaying module (not shown) used to display the blood pressure value.

The aforementioned embodiments are only preferred embodiments of the present application. For one of ordinary skill in the art, according to the thought of the present application, specific implementation modes and application scopes may be modified, and the content of the specification should not be interpreted as any limitation to the present application.

What is claimed is:

1. An optical fiber blood pressure continuous detection wristband for detecting a blood pressure, comprising:
    a wristband assembly, configured to be worn on a wrist and comprising: an inner wristband and an outer wristband that are mutually engageable, wherein when the inner wristband and the outer wristband are fully engaged, an engaged portion of the inner wristband is configured to be placed adjacent to the wrist relative to the outer wristband;
    an optical fiber sensing assembly module, disposed on a surface of the inner watchband wristband away from the outer wristband; wherein the optical fiber sensing assembly module comprises a sensing band and an optical fiber configured to extend along the sensing band and form a sensing area to sense a pulse wave; wherein the sensing band comprises an inner layer having a first surface and a second surface opposite to the first surface, with the second surface being configured to be placed adjacent to the wrist, and the first surface being abutted against the optical fiber; and an outer layer having a third surface and a forth surface opposite to the third surface, with the third surface being provided with a first concave-convex structure with a corrugate shape, the first concave-convex structure being abutted against the optical fiber; wherein a space is formed between the sensing band and the inner wristband and configured for the radial artery to beat;
    a calibration assembly, configured to detect a blood pressure of the wrist in conjunction with the optical fiber sensing assembly module, and configured to continuously calibrate a blood pressure value detected by the optical fiber sensing assembly module using one hand; and
    a signal process assembly, connected between the inner wristband and the outer wristband, and configured to convert a luminous decay signal generated by the decay of a light signal passing through the optical fiber into an electric charge so as to calculate the pulse wave,
    wherein the outer wristband is provided with a signal reinforcing area corresponding to the optical fiber sensing assembly module, and the signal reinforcing area is provided with a plurality of bulges protruding toward the inner wristband.

2. The optical fiber blood pressure continuous detection wristband of claim 1, wherein an outer surface of the sensing band is covered by a stretchable adjustable layer.

3. The optical fiber blood pressure continuous detection wristband of claim 1, wherein the plurality of bulges are arranged in a regular array on the signal reinforcing area.

4. The optical fiber blood pressure continuous detection wristband of claim 1, wherein the signal process assembly comprises:
    a control circuit, configured to electrically connected to the calibration assembly;
    an optical fiber connector portion comprising an output portion and an input portion; an LED light source component;
    and an optical fiber sensing component;
    wherein the LED light source component is electrically connected to the control circuit via the input portion, and the optical fiber sensing component is electrically connected to the control circuit via the output portion.

5. The optical fiber blood pressure continuous detection wristband of claim 4, wherein the signal process assembly further comprises:
    an optical detecting module, configured to receive the light decay signal of the optical fiber;
    a signal calculating and processing module, configured to convert the light decay signal of the optical fiber into electric charge so as to calculate the pulse wave;

a blood pressure calibrating module, configured to process, analyze and calculate the pulse wave in order to obtain the blood pressure value;

a memory module, configured to store the blood pressure value; and a displaying module, configured to display the blood pressure value.

6. The optical fiber blood pressure continuous detection wristband of claim 5, wherein the calibration assembly is arranged on the signal process assembly and comprises: a first electrode, disposed on an outer surface of the displaying module; and a second electrode, disposed on an inner surface of the signal process assembly and configured to be attached to the wrist, such that the first electrode, the second electrode and a subject form a closed loop for detecting electrocardiograph signals.

7. The optical fiber blood pressure continuous detection wristband of claim 1, wherein the shape of the first concave-convex structure is one of a group of a triangular corrugated shape, a circular corrugated shape, a quadrate corrugated shape, and a trapezoidal corrugated shape, or any combination of the triangular corrugated shape, the circular corrugated shape, the quadrate corrugated shape, or the trapezoidal corrugated shape thereof.

8. The optical fiber blood pressure continuous detection wristband of claim 7, wherein the second surface is provided with a second concave-convex structure, the shape of the second concave-convex structure is one of a group of a triangular corrugated shape, a circular corrugated shape, a quadrate corrugated shape, and a trapezoidal corrugated shape, or any combination of the triangular corrugated shape, the circular corrugated shape, the quadrate corrugated shape, or the trapezoidal corrugated shape thereof.

9. The optical fiber blood pressure continuous detection wristband of claim 8, wherein the optical fiber comprises optical fiber rows having a plurality of serially connected U-shaped or S-shaped fiber cable extended along the longitudinal direction or width direction of the sensing band.

10. The optical fiber blood pressure continuous detection wristband of claim 8, wherein the optical fiber comprises optical fiber rows having a plurality of serially connected O-shaped fiber cable extended along the longitudinal direction or width direction of the sensing band.

11. The optical fiber blood pressure continuous detection wristband of claim 9, wherein at least two optical fiber rows are superposed vertically, and bend parts of the fiber cable of the vertically superposed optical fiber cable rows are staggered.

12. The optical fiber blood pressure continuous detection wristband of claim 9, wherein at least two optical fiber rows are superposed vertically, and bend parts of the fiber cable of the vertically superposed optical fiber cable rows are arranged in a criss-cross pattern.

13. The optical fiber blood pressure continuous detection wristband of claim 10, wherein at least two optical fiber rows are superposed vertically, and bend parts of the fiber cable of the vertically superposed optical fiber cable rows are staggered.

14. The optical fiber blood pressure continuous detection wristband of claim 10, wherein at least two optical fiber rows are superposed vertically, and bend parts of the fiber cable of the vertically superposed optical fiber cable rows are arranged in a criss-cross pattern.

15. A wearing apparatus, comprising:

an optical fiber blood pressure continuous detection wristband and an electronic circuit module electrically connected to the optical fiber blood pressure continuous detection wristband, wherein the optical fiber blood pressure continuous detection wristband comprises:

a wristband assembly, configured to be worn on a wrist and comprising: an inner wristband and an outer wristband that are mutually engageable, wherein when the inner wristband and the outer wristband are fully engaged, an engaged portion of the inner wristband is configured to be placed adjacent to the wrist relative to the outer wristband;

an optical fiber sensing assembly module, disposed on along a surface of the inner wristband away from the outer wristband; wherein the optical fiber sensing assembly module comprises a sensing band and an optical fiber configured to extend along the sensing band and form a sensing area to sense a pulse wave; wherein the sensing band comprises an inner layer having a first surface and a second surface opposite to the first surface, with the second surface of being configured to be placed adjacent to the wrist, and the first surface being abutted against the optical fiber; and an outer layer having a third surface and a forth surface opposite to the third surface, with the third surface being provided with a first concave-convex structure with a corrugate shape, the first concave-convex structure being abutted against the optical fiber; wherein a space is formed between the sensing band and the inner wristband and configured for the radial artery to beat;

a calibration assembly, configured to detect a blood pressure of the wrist in conjunction with the optical fiber sensing assembly module, and configured to continuously calibrate a blood pressure value detected by the optical fiber sensing assembly module using one hand; and a signal process assembly, connected between the inner wristband and the outer wristband, and configured to convert a luminous decay signal generated by the decay of a light signal passing through the optical fiber into an electric charge so as to calculate the pulse wave, wherein the outer wristband is provided with a signal reinforcing area corresponding to the optical fiber sensing assembly module, and the signal reinforcing area is provided with a plurality of bulges protruding toward the inner wristband.

16. The wearing apparatus of claim 15, wherein the electronic circuit module comprises:

a display unit, configured for human-computer interaction and displaying the detected blood pressure value; and a calculating and processing module unit, configured to process light decay changes and estimate pulse pressure changes of the radial artery.

17. An optical fiber blood pressure continuous detection wristband for detecting a blood pressure, comprising:

a wristband assembly, configured to be worn on a wrist and comprising: an inner wristband and an outer wristband that are mutually engageable, wherein when the inner wristband and the outer wristband are fully engaged, an engaged portion of the inner wristband is configured to be placed adjacent to the wrist relative to the outer wristband;

an optical fiber sensing assembly module, disposed on a surface of the inner wristband away from the outer wristband; wherein the optical fiber sensing assembly module comprises a sensing band and an optical fiber configured to extend along the sensing band and form a sensing area to sense a pulse wave; wherein the sensing band comprises an inner layer having a first surface and a second surface opposite to the first surface, with the second surface being configured to be placed adjacent to the wrist, and the first surface being abutted against the optical fiber; and an outer layer having a third surface and a fourth surface opposite to the third surface, with the third surface being provided with a first concave-convex structure with a corrugate shape, the first concave-convex structure being abutted against the optical fiber; wherein a space is formed between the sensing band and the inner wristband and configured for the radial artery to beat;

a calibration assembly, configured to detect a blood pressure of the wrist to be detected in conjunction with the optical fiber sensing assembly module, and configured to continuously calibrate a blood pressure value detected by the optical fiber sensing assembly module using one hand; and signal process assembly, connected between the inner wristband and the outer wristband, and configured to convert a luminous decay signal generated by the decay of a light signal passing through the optical fiber into an electric charge so as to calculate the pulse wave;

wherein the signal process assembly comprises:

a control circuit, configured to electrically connected to the calibration assembly; an optical fiber connector portion comprising an output portion and an input portion; an LED light source component; and an optical fiber sensing component; wherein the LED light source component is electrically connected to the control circuit via the input portion, and the optical fiber sensing component is electrically connected to the control circuit via the output portion.

\* \* \* \* \*